(12) United States Patent
Matsumoto et al.

(10) Patent No.: US 9,901,456 B2
(45) Date of Patent: Feb. 27, 2018

(54) VERTEBRAL BODY SPACER

(75) Inventors: Toshio Matsumoto, Tokyo (JP); Yuzo Daigo, Kitamoto (JP); Shinichi Ohmori, Kitamoto (JP); Komei Kato, Saitama (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 0 days.

(21) Appl. No.: 13/884,439

(22) PCT Filed: Nov. 9, 2011

(86) PCT No.: PCT/JP2011/075836
§ 371 (c)(1),
(2), (4) Date: Jul. 3, 2013

(87) PCT Pub. No.: WO2012/063865
PCT Pub. Date: May 18, 2012

(65) Prior Publication Data
US 2013/0274886 A1    Oct. 17, 2013

(30) Foreign Application Priority Data
Nov. 10, 2010    (JP) .................................. 2010-252229

(51) Int. Cl.
*A61F 2/44*    (2006.01)
*A61F 2/30*    (2006.01)

(52) U.S. Cl.
CPC ............ *A61F 2/442* (2013.01); *A61F 2/4465* (2013.01); *A61F 2002/30011* (2013.01);
(Continued)

(58) Field of Classification Search
CPC ................ A61F 2/442; A61F 2002/445; A61F 2002/4445; A61F 2/4455; A61F 2/447
(Continued)

(56) References Cited

U.S. PATENT DOCUMENTS 5,458,643 A    10/1995    Oka et al.
6,379,385 B1    4/2002    Kalas et al.
(Continued)

FOREIGN PATENT DOCUMENTS

EP    1477190 A1    11/2004
EP    2453937 A2    5/2012
(Continued)

OTHER PUBLICATIONS

International Search Report dated Feb. 14, 2012, issued for PCT/JP2011/075836.

*Primary Examiner* — Ellen C Hammond
*Assistant Examiner* — Christina Nehrellirodrigue
(74) *Attorney, Agent, or Firm* — Locke Lord LLP

(57) ABSTRACT

A vertebral body spacer of the present invention is used by being inserted between a vertebral body and a vertebral body (intervertebral space). The vertebral body spacer has a block body constituted of titanium or a titanium alloy as a main component thereof, and provided with a pair of contact surfaces to be made contact with the vertebral body and the vertebral body. The block body includes dense sheets having a dense part on at least a surface thereof and porous sheets having a porous part on at least a surface thereof. The porous part has a larger porosity than a porosity of the dense part. Each of the porous sheets is sandwiched between the pair of dense sheets. According to the present invention, it is possible to maintain an appropriate size between the vertebral bodies (intervertebral space).

14 Claims, 12 Drawing Sheets

(52) U.S. Cl.
CPC ............ *A61F 2002/30013* (2013.01); *A61F 2002/3097* (2013.01); *A61F 2002/30471* (2013.01); *A61F 2002/30472* (2013.01); *A61F 2002/30492* (2013.01); *A61F 2002/30616* (2013.01); *A61F 2002/30841* (2013.01); *A61F 2002/30892* (2013.01); *A61F 2002/30967* (2013.01); *A61F 2002/30968* (2013.01); *A61F 2002/30971* (2013.01); *A61F 2002/448* (2013.01); *A61F 2310/00023* (2013.01); *A61F 2310/00431* (2013.01); *A61F 2310/00443* (2013.01); *A61F 2310/00485* (2013.01); *A61F 2310/00491* (2013.01); *A61F 2310/00497* (2013.01); *A61F 2310/00514* (2013.01); *A61F 2310/00532* (2013.01); *A61F 2310/00544* (2013.01); *A61F 2310/00562* (2013.01); *A61F 2310/00976* (2013.01)

(58) Field of Classification Search
USPC .................. 623/17.11–17.16; 606/246–249
See application file for complete search history.

(56) References Cited

U.S. PATENT DOCUMENTS

| | | | |
|---|---|---|---|
| 6,423,095 | B1 | 7/2002 | Van Hoeck et al. |
| 8,119,152 | B2 | 2/2012 | Shikinami |
| 8,361,150 | B2 * | 1/2013 | Zhang et al. ............. 623/17.11 |
| 2001/0001129 | A1 | 5/2001 | McKay et al. |
| 2001/0010021 | A1 * | 7/2001 | Boyd et al. ............. 623/17.13 |
| 2002/0169066 | A1 | 11/2002 | Cassidy et al. |
| 2004/0010312 | A1 | 1/2004 | Enayati |
| 2004/0258732 | A1 | 12/2004 | Shikinami |
| 2005/0038513 | A1 | 2/2005 | Michelson |
| 2005/0049706 | A1 | 3/2005 | Brodke et al. |
| 2005/0065604 | A1 | 3/2005 | Stoll |
| 2005/0159815 | A1 | 7/2005 | Kamimura et al. |
| 2006/0173542 | A1 * | 8/2006 | Shikinami ............ A61F 2/30965 623/14.12 |
| 2009/0162235 | A1 | 6/2009 | Kita et al. |
| 2009/0204214 | A1 | 8/2009 | Fuji et al. |
| 2009/0317278 | A1 | 12/2009 | Kokubo |
| 2011/0054616 | A1 | 3/2011 | Kamran et al. |
| 2011/0190888 | A1 * | 8/2011 | Bertele ................ A61F 2/446 623/17.11 |

FOREIGN PATENT DOCUMENTS

| | | |
|---|---|---|
| JP | 04-303444 A | 10/1992 |
| JP | 10-033656 A | 2/1998 |
| JP | 2001-046489 A | 2/2001 |
| JP | 2002-095685 A | 4/2002 |
| JP | 2003-230583 A | 8/2003 |
| JP | 2004-081257 A | 3/2004 |
| JP | 2004-337277 A | 12/2004 |
| JP | 2005-529634 A | 10/2005 |
| JP | 2007-151805 A | 6/2007 |
| JP | 2007-236803 A | 9/2007 |
| JP | 2009-207878 A | 9/2009 |
| WO | WO-2008/026316 A1 | 3/2008 |
| WO | WO-2010/019799 A1 | 2/2010 |
| WO | WO-2010/021612 A1 | 2/2010 |
| WO | WO-2011/008733 A2 | 1/2011 |

* cited by examiner

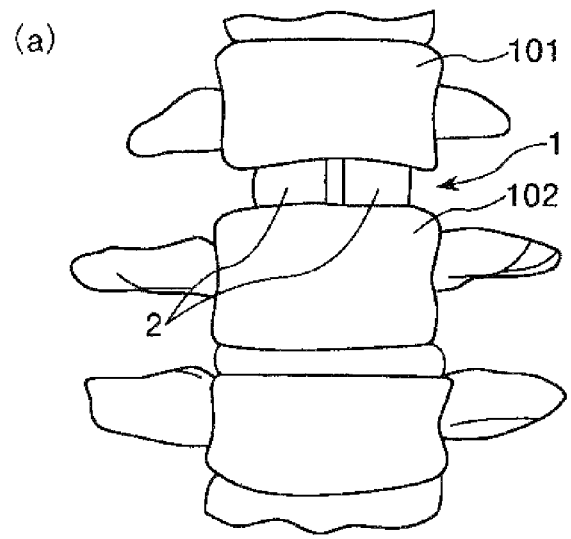
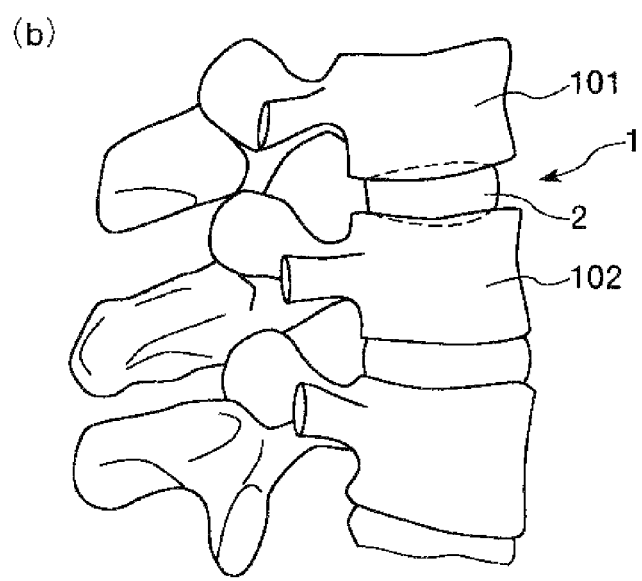
FIG.2

VERTEBRAL BODY SPACER

CROSS REFERENCE TO RELATED APPLICATIONS

This application is related to co-pending application, entitled, "VERTEBRAL BODY SPACER" filed concurrently herewith in the names of Toshio Matsumoto, Yuzo Daigo, Shinichi Ohmori and Komei Kato as a national stage application of International Application Nos. PCT/JP2011/075841 and PCT/JP2011/075832 filed Nov. 9, 2011, which application is assigned to the assignee of the instant application and which co-pending application is also incorporated by reference herein.

TECHNICAL FIELD

The present invention relates to a vertebral body spacer.

RELATED ART

Spinal canal stenosis is caused by degeneration of an intervertebral disk interposed between adjacent vertebral bodies (intervertebral space), degenerative facet joint disease, secondary deformation of a vertebral body, spinal deformation, or the like, and results in cauda equina/nerve root disorders.

One approach for treating such spinal canal stenosis includes interbody fusion in which a degenerated intervertebral disk is removed from between the adjacent vertebral bodies, and then used is an vertebral body fusion surgery of fusing the vertebral bodies by implanting an autologous bone into an intervertebral space in which the intervertebral disk has been removed.

However, in a case where only bone grafting into the intervertebral space is carried out, there is a possibility that unstable fusing between the vertebral bodies is caused by resorption of a grafted bone until bone fusion is achieved. Further, an amount capable of harvesting an autologous bone is limited, so that there is a possibility that a bone to be grafted is not acquired in a sufficient amount.

Therefore, used is a method of fusing the vertebral bodies stably by inserting a vertebral body spacer by itself as a substitute material of an autologous bone or the vertebral body spacer together with the autologous bone into an intervertebral space.

In this case, it is required that this vertebral body spacer supports vertebral bodies stably and fuses with the vertebral bodies easily. From a point of such a view, a constituent material and a shape of the vertebral body spacer have been studied, so that various kinds of vertebral body spacers have been developed (for example, Patent Document 1).

Such a vertebral body spacer, generally, is constituted from a block body having a uniform porosity. Such a porosity is set to fall within the range of about 30 to 60% for a purpose of achieving bone fusion between the vertebral body spacer and vertebral bodies making contact with the vertebral body spacer promptly.

However, it is impossible for the vertebral body spacer having the porosity falling within such a range to withstand stress on the vertebral body spacer depending on a body type of a patient to which the spacer is to be applied and a position of an intervertebral space such as lumbar vertebra and cervical vertebra. As a result, there is a fear that the vertebral body spacer is broken by the stress.

Patent Document: JP 2002-95685 A

SUMMARY OF THE INVENTION

It is an object of the present invention to provide a vertebral body spacer that is capable of maintaining an appropriate size between vertebral bodies (intervertebral space) and reliably preventing the vertebral body spacer from being broken irrespective of cases and a position of the intervertebral space, and thereby capable of achieving bone fusion between the vertebral body spacer and vertebral bodies promptly.

The object is achieved by the present inventions (1) to (11) described below;

(1) A vertebral body spacer to be used by being inserted between vertebral bodies, comprising;

at least one block body constituted of titanium or a titanium alloy as a main component thereof, and the block body having a pair of contact surfaces to be made contact with the vertebral bodies, respectively, wherein the block body includes a plurality of first sheet parts and a plurality of second sheet parts which are arranged alternately, wherein one of the first sheet parts and the second sheet parts is constituted from dense sheets each having a dense part on at least a peripheral portion thereof, the other of the first sheet parts and the second sheet parts is constituted from porous sheets each having a porous part on at least a peripheral portion thereof, and the dense parts and the porous parts form the contact surfaces, wherein the porous part has a larger porosity than a porosity of the dense part.

This makes it possible to maintain an appropriate size between the vertebral bodies (intervertebral space). Further, it is possible to reliably prevent the block body from being broken irrespective of cases and a position of the intervertebral space, and thereby capable of achieving bone fusion between the block body and the vertebral bodies promptly.

(2) In the vertebral body spacer in above-mentioned item (1), the first sheet parts are constituted from the dense sheets and the second sheet parts are constituted from the porous sheets.

This makes it possible to sandwich the porous sheet between the two dense sheets, thereby reliably suppressing or preventing stress from being applied to the porous sheet.

(3) In the vertebral body spacer in above-mentioned item (1), the first sheet parts and the second sheet parts are formed integrally.

According to the vertebral body spacer mentioned above, in a state of inserting the block body into the intervertebral space, it is possible to reliably prevent the stress from being applied to the dense sheets or the porous sheet unevenly when the stress is applied to the block body.

(4) In the vertebral body spacer in above-mentioned item (1), the block body is constituted from a polyhedral body defined by a plurality of surfaces including the pair of contact surfaces, and each of the plurality of surfaces constitutes a flat surface.

This makes it possible to reliably make the porous sheets contact with the vertebral bodies. Therefore, it is possible to achieve the bone fusion between the porous sheets and the vertebral bodies promptly.

(5) In the vertebral body spacer in above-mentioned item (1), a whole of each of the porous sheets is constituted from the porous part.

This makes it possible to achieve the bone fusion between the porous sheets and vertebral bodies promptly. Therefore, it is possible to reliably fuse the block body in the intervertebral space.

(6) In the vertebral body spacer in above-mentioned item (1), a whole of each of the dense sheets is constituted from the dense part.

According to this vertebral body space mentioned above, the dense sheets exhibit more excellent strength. Therefore, it is possible to reliably prevent or suppress the block body from being broken in a state of inserting the block body into the intervertebral space.

(7) In the vertebral body spacer in above-mentioned item (1), an osteoinductive factor is carried on the porous part.

This makes it possible to achieve the bone fusion between the porous sheets and the vertebral bodies promptly.

(8) In the vertebral body spacer in above-mentioned item (1), the block body is formed into an elongated shape, and a direction in which the plurality of first sheet parts and the plurality of second sheet parts are arranged is a longitudinal direction of the block body.

According to this vertebral body spacer mentioned above, the dense sheets and the porous sheets become in contact with the vertebral bodies alternately in the state of inserting the block body into the intervertebral space. Therefore, even if the stress is applied to the block body in this state, it is possible to reliably maintain the shape of the block body due to the dense sheets. As a result, it is possible to reliably prevent or suppress the porous sheets from being broken while maintaining the appropriate size of the intervertebral space. Further, since it is ensured to achieve the bone fusion between the porous sheets and the vertebral bodies promptly, the block body is fused in the intevertebral space reliably.

(9) In the vertebral body spacer in above-mentioned item (1), the block body is formed into an elongated shape, and a direction in which the plurality of first sheet parts and the plurality of second sheet parts are arranged is a short direction of the block body and a direction substantially perpendicular to a direction from one toward the other of the contact surfaces.

According to this vertebral body spacer mentioned above, the dense sheets and the porous sheets become in contact with the vertebral bodies alternately in the state of inserting the block body into the intervertebral space. Therefore, even if the stress is applied to the block body in this state, it is possible to reliably maintain the shape of the block body due to the dense sheets. As a result, it is possible to reliably prevent or suppress the porous sheets from being broken while maintaining the appropriate size of the intervertebral space. Further, since it is ensured to achieve the bone fusion between the porous sheets and the vertebral bodies promptly, the block body is fused in the intevertebral space reliably.

(10) In the vertebral body spacer in above-mentioned item (1), the block body is formed into an elongated shape, and a direction in which the plurality of first sheet parts and the plurality of second sheet parts are arranged is a short direction of the block body and a direction substantially parallel to a direction from one toward the other of the contact surfaces.

(11) In the vertebral body spacer in above-mentioned item (1), at least one block body is constituted from a pair of block bodies.

This makes it possible to change a position of a pair of block bodies, namely to position the pair of block bodies in a state of spacing front ends and back ends of the pair of block bodies from each other and/or approaching them to each other. Therefore, it is possible to provide an appropriate cure depending on cases by using such a vertebral body spacer.

According to the vertebral body spacer of the present invention, it is capable of maintaining the appropriate size between vertebral bodies (intervertebral space). Further, it is possible to reliably prevent the vertebral body spacer from being broken irrespective of the cases and the position of the intervertebral space, and thereby capable of achieving the bone fusion between the vertebral body spacer and the vertebral bodies promptly.

Further, by inserting the vertebral body spacer into the intervertebral space, it is ensured to obtain a space for filling a filler into the intervertebral space. Therefore, by filling, for example, a grafted bone into such a space, it is possible to achieve the bone fusion between the vertebral bodies through the vertebral body spacer and the grafted bone more reliably and promptly.

BRIEF DESCRIPTION OF THE DRAWINGS

FIG. 2 is a view showing a used state of the first embodiment of the vertebral body spacer of the present invention.

BEST MODE FOR CARRYING OUT THE INVENTION

Hereinbelow, description will be made on a vertebral body space according to the present invention in detail with reference to preferred embodiments shown accompanied drawings.

<First Embodiment>

First, description will be made on a first embodiment of a vertebral body space according to the present invention.

Figure 1:
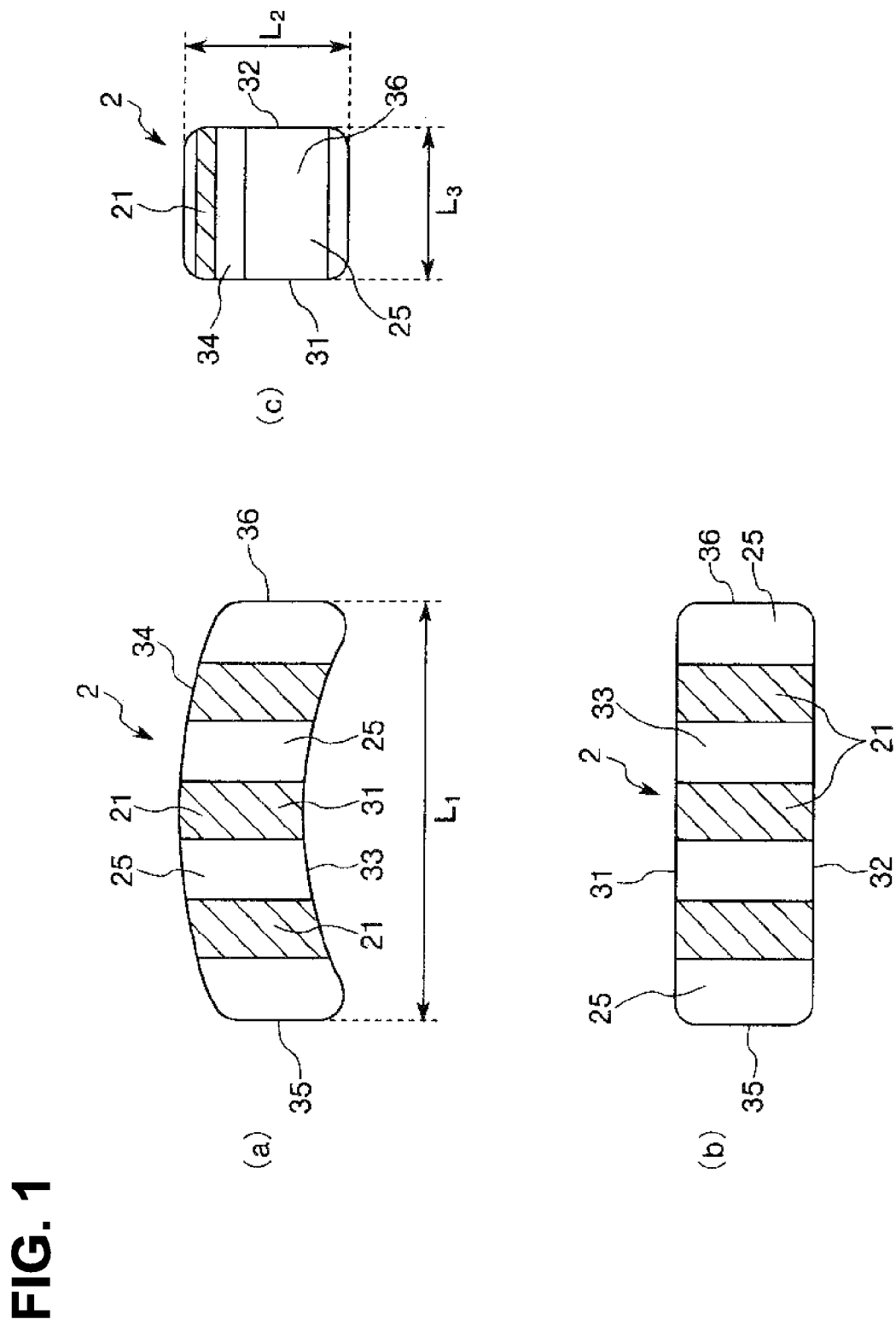
FIG. 1 is a plan view (a), a front view (b) and a side view (c) which show a first embodiment of a block body constituting a vertebral body spacer of the present invention.
Figure 3:
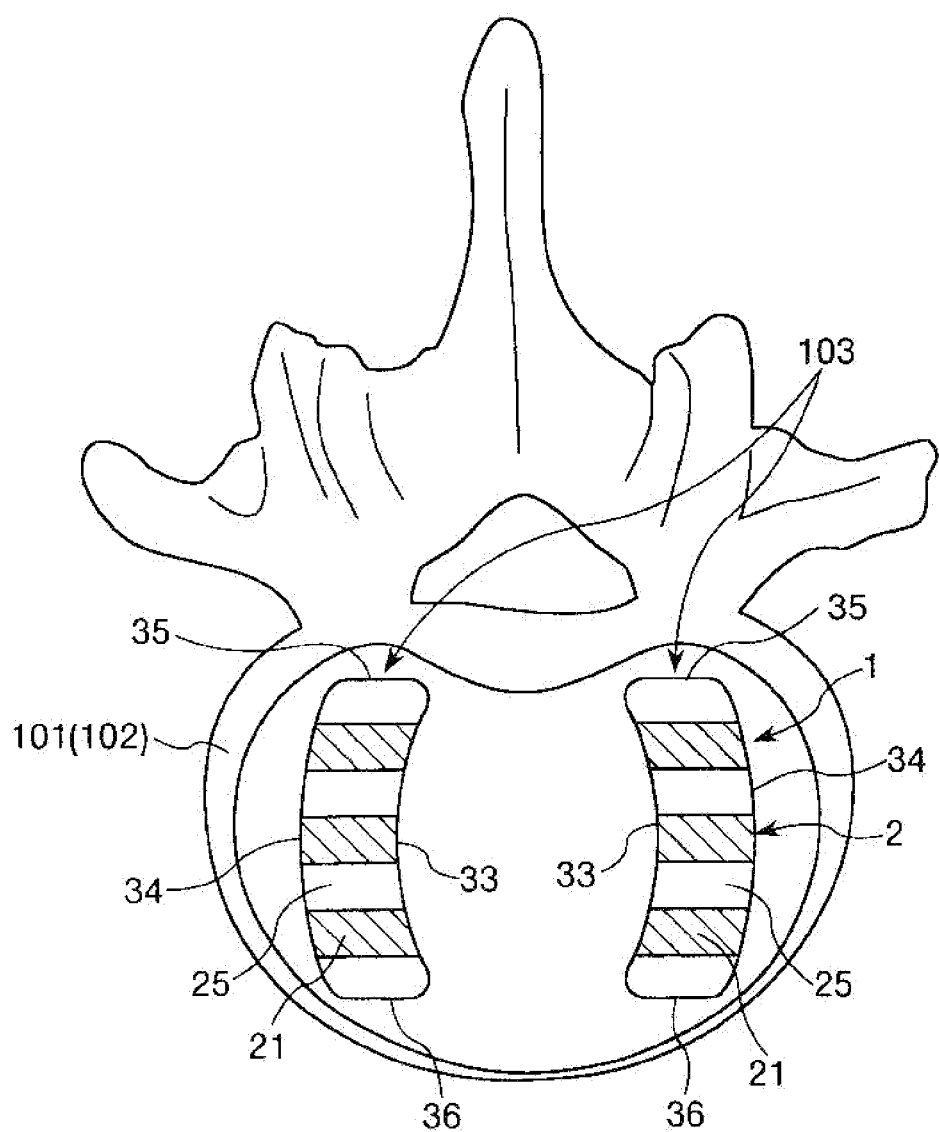
FIG. 3 is a view showing a used state of the first embodiment of the vertebral body spacer of the present invention.

FIG. 1 is a plan view (a), a front view (b) and a side view (c) which show the first embodiment of a block body constituting the vertebral body spacer of the present invention. FIG. 2 and FIG. 3 are a view showing a used state of the first embodiment of the vertebral body spacer of the present invention, respectively.

In the following description, it is to be noted that a state of inserting the vertebral body spacer between vertebral bodies of a case (patient) is defined as a basic state, thereby identifying a position thereof, unless it is explicitly stated otherwise.

Specifically, a ventral side of the patient (namely, a right side in each of FIG. 1(a), FIG. 1(b) and FIG. 2(b), a near side in each sheet of FIG. 1(c) and FIG. 2(a), and a lower side in FIG. 3) will be referred to as "front", and a dorsal side of the patient (namely, a left side in each of FIG. 1(a), FIG. 1(b) and FIG. 2(b), a back side in each sheet of FIG. 1(c) and FIG. 2(a), and an upper side in FIG. 3) will be referred to as "back". Further, a head side of the patient (namely, an upper side in each of FIG. 1(b) and FIG. 2, a near side in each sheet of FIG. 1(a) and FIG. 3, and a left side in FIG. 1(c)) will be referred to as "upper", and a leg side of the patient (namely, a lower side in each of FIG. 1(b) and FIG. 2, a back side in each sheet of FIG. 1(a) and FIG. 3, and a right side in FIG. 1(c)) will be referred to as "lower". It is to be noted that a position of the vertebral body spacer in each of FIGS. 4 to 12 is also defined as the same as those in FIGS. 1 to 3.

As shown in FIG. 2, a vertebral body spacer 1 is inserted between a vertebral body 101 and a vertebral body 102 (hereinafter, referred to as "intervertebral space") at the time of fusing the upper vertebral body 101 and the lower vertebral body 102 after an intervertebral disk has been removed. It is ensured to maintain (hold) an appropriate space (distance) between the vertebral body 101 and the vertebral body 102 in a state of inserting the vertebral body spacer 1 into the intervertebral space (hereinafter, referred to as "inserted state").

In this regard, it is to be noted that the FIG. 1 and FIG. 3 have been hatched for easy understanding of differences between porous sheets 21 and dense sheets 25, and the hatchings do not mean cross section surfaces.

In the present embodiment, as shown in FIG. 2(a) and FIG. 3, the vertebral body spacer 1 (hereinafter, simply referred to as "spacer 1") is constituted from a pair of elongated block bodies 2, 2. Each of the block bodies 2, 2 is substantially identical to each other in a shape (constitution).

As described above, each of the block bodies 2, 2 is substantially identical to each other in the shape. Therefore, hereinafter, the description will be made on one of the pair of elongated block bodies 2, 2 as a representative.

As shown in FIG. 1, the block body 2 is constituted from a polyhedral body which is formed from a plurality of surfaces having a first surface 31, a second surface 32, a third surface 33, a fourth surface 34, a fifth surface 35 and a sixth surface 36.

As shown in FIG. 3, the first surface 31 constitutes a contact surface to be made contact with the vertebral body 101 and the second surface 32 constitutes a contact surface to be made contact with the vertebral body 102 in a state of inserting the block body 2 into the intervertebral space (inserted state). Further, in the inserted state, the third surface 33 defines an inside space 103 in the intervertebral space and the fourth surface 34 defines an outside space 103 in the intervertebral space.

In the present embodiment, the third surface 33 constitutes a curved concave surface and the fourth surface constitutes a curved convex surface. This makes it possible to easily insert the block body 2 into the intervertebral space so as to correspond to shapes of the vertebral bodies (vertebral bone).

Further, the first surface 31, the second surface 32, the fifth surface 35 and the sixth surface 36 constitute substantially a plane surface (flat surface), respectively. Among of them, in particular, the plane surfaces (flat surfaces) of the first surface 31 and the second surface 32 make it possible to reliably be in the block body 2 contact with the vertebral bodies 101, 102.

Further, the first surface 31 and the second surface 32 have substantially an equal length. The third surface 33 and the fourth surface 34 also have substantially an equal length. The fifth surface 35 and the sixth surface 36 also have substantially an equal length.

In other words, the block body 2 is formed so that a cuboid is curved along a longitudinal direction thereof so as to concave the third surface 33 and convex the fourth surface 34.

In this regard, the vicinities of corner portions formed by making contact with each surface are chamfered, respectively. This makes it possible to prevent breakages such as a crack of the block body 2. In addition to that, it is possible to easily insert the block body 2 into the intervertebral space with making no contact with the vertebral bodies 101 and 102.

Dimension such as the length of such a block body 2 in a front-back direction ($L_1$ in FIG. 1), the length thereof in a horizontal direction ($L_2$ in FIG. 1) and the length thereof in an upper-lower direction ($L_3$ in FIG. 1) is arbitrarily dependent from a kind of vertebral body such as cervical vertebra and lumbar vertebra or cases. The dimension, however, is set to fall within ranges as follows.

The length of such a block body 2 in the front-back direction ($L_1$ in FIG. 1) is preferably set to the range of about 6 to 25 mm and more preferably the range of about 8 to 22 mm.

The length of the block body 2 in the horizontal direction ($L_2$ in FIG. 1) is preferably set to the range of about 4 to 25 mm, more preferably the range of about 10 to 25 mm and even more preferably the range of about 16 to 21 mm.

The length of the block body 2 in the upper-lower direction ($L_3$ in FIG. 1) is preferably set to the range of about 6 to 15 mm and more preferably the range of about 9 to 12 mm.

Meanwhile, the block body 2 having such a configuration of the present invention includes a pair of first sheet parts and second sheet parts each sandwiched between the pair of first sheet parts. One of the first sheet parts and the second sheet parts is constituted from dense sheets each having a dense part on at least a surface thereof. The other of the first sheet parts and the second sheet parts is constituted from porous sheets each having a porous part on at least a surface thereof. A porosity of such a porous part is larger than a porosity of the dense part. This configuration makes it possible to maintain a shape of the block body 2 due to the existence of the dense sheets even if the stress is applied to the block body 2 in the state of inserting the block body 2 into the intervertebral space (inserted state). Therefore, it is possible to reliably prevent or suppress the porous sheets from being broken while maintaining the appropriate size of the intervertebral space. Further, it is ensured to achieve the bone fusion between the vertebral bodies 101, 102 and the porous sheets promptly.

The block body 2 of the present embodiment is constituted from four dense sheets 25 and three porous sheets 21. One porous sheet 21 is sandwiched between a pair of dense sheets 25. In other words, in the present embodiment, the dense sheets 25 constitute the first sheet parts and the porous sheets 21 constitute the second sheet parts. A direction (arranging direction) in which the dense sheets 25 and the porous sheets 21 are arranged is a direction from a front side toward a back side, namely a longitudinal direction of the block body 2.

The dense sheets 25 and the porous sheets 21 in the block body 2 of the configuration are formed so as to correspond to a cross-section shape thereof when the block body 2 is cut in a direction perpendicular to the direction from the front side toward the back side thereof (longitudinal direction).

The dense sheets 25 and the porous sheets 21 in the block body 2 having such a configuration become in contact with the vertebral bodies 101, 102 alternately in the inserted state. Therefore, even if the stress is applied to the block body 2 in this state, it is possible to reliably maintain the shape of the block body 2 due to the dense sheets 25. As a result, it is possible to reliably prevent or suppress the porous sheets 21 from being broken while maintaining the appropriate size of the intervertebral space. Further, since it is ensured to achieve the bone fusion between the porous sheets 21 and the vertebral bodies 101, 102 promptly, the block body 2 is fused in the intevertebral space reliably.

In the present embodiment, the dense sheets 25 are constituted from the dense part (dense body) in a substantial whole thereof. By this configuration, the dense sheets 25 are capable of exhibiting more excellent strength. Therefore, in the inserted state, it is possible to reliably prevent or suppress the block body 2 from being broken. In this regard, the porosity of the dense part is not limited particularly as long as the porosity of the dense part is lower than the porosity of the porous part of the porous sheets 21. Specifically, the porosity of the dense part is preferably in the range of about 3 to 50%, more preferably in the range of about 10 to 40% and even more preferably in the range of about 15 to 35%. It is to be noted that the porosity of the dense part may be substantially 0%.

Further, the porous sheets 21 in the present embodiment are constituted from the porous part (porous body) having the larger porosity than the porosity of the dense part in the substantial whole thereof. Specifically, the porosity of the porous sheets 21 is in the range of about 20 to 95%, more preferably in the range of about 50 to 85% and even more preferably in the range of about 55 to 85%. This makes it possible to achieve the bone fusion between the vertebral bodies 101, 102 and the porous sheets 21 promptly. In the case where the porosity of the porous sheets 21 falls within such ranges, it is possible to reliably prevent or suppress the block body 2 from being broken when the stress is applied to the block body 2 in the inserted state. This is because the block body 2 has the dense sheets 25 in addition to the porous sheets 21. In this regard, it is to be noted that it is easy to form communicating holes, in which holes are connected with each other, in the porous sheets 21 if the porosity of the porous sheets 21 is equal to or larger than 55%.

A thickness of each of the dense sheets 25 is not limited particularly, but preferably in the range of about 1 to 6 mm and more preferably in the range of about 2 to 4 mm. A thickness of each of the porous sheets 21 is also not limited particularly, but preferably in the range of about 0.5 to 3 mm and more preferably in the range of about 1 to 2 mm.

Further, when the thickness of each of the dense sheets 25 is defined as A [mm] and the thickness of each of the porous sheets 21 is defined as B [mm], the A/B satisfies preferably a relation being in the range of 1 to 4, and more preferably a relation being in the range of 2 to 4. By satisfying the relations, it becomes possible to reliably exhibit both effects of preventing the breakage of the block body 2 in the inserted state and achieving the bone fuse between the block body 2 and vertebral bodies 101, 102 promptly.

Particularly, in the present embodiment, sheets located at both end portions of the block body 2 are constituted from the dense sheets 25. In other words, each of the porous sheets 21 are sandwiched between a pair of dense sheets 25 necessarily. Therefore, since each of the porous sheets 21 are sandwiched with the two dense sheets 25, it is possible to reliably suppress or prevent stress from being applied to the block body 2 in the inserted state.

Further, it is preferred that an osteoinductive factor is carried on inner surfaces of the communicating holes (holes) of the porous sheets 21 (porous part). This makes it possible to achieve the bone fusion between the vertebral bodies 101, 102 and the porous sheets 21 promptly.

The osteoinductive factor is not limited particularly as long as it has an activity of promoting bone formation by deriving differentiated osteoblast from an undifferentiated mesenchymal cell. Specifically, bone morphogenic protein (BMP) is used preferably as the osteoinductive factor.

Examples of BMP include BMP-1, BMP-2, BMP-3, BMP-4, BMP-5, BMP-6, BMP-7, BMP-8, BMP-9, BMP-12 (these are a homodimer), a heterodimer of their BMPs or a modified body thereof, and the like.

In the present invention, the block body 2 can be produced by using a producing method as described later. According to such a producing method, it is possible to form the dense sheets 25 and the porous sheets 21 integrally. Such a block body 2 is capable of reliably preventing the stress from unevenly being applied to the dense sheets 25 or the porous sheets 21 when the stress is applied in the inserted state. In this case, each of surfaces 31, 32, 33, 34 constitutes a flat surface, namely a surface having no gap between the dense sheets 25 and the porous sheets 21. Therefore, it is possible to particularly make the porous sheets 21 contact with the vertebral bodies 101, 102 in the first surface 31 and the second surface 32. Consequently, it is possible to achieve the bone fusion between the vertebral bodies 101, 102 and the porous sheets 21 promptly.

In the present invention, a titanium based material such as titanium or a titanium alloy is mainly used as a constituent material of such a block body 2, namely constituent materials of the dense sheets 25 and the porous sheets 21.

The titanium based material has high biocompatibility and excellent strength, and therefore is used as the constituent material of the block body 2 reliably. In the titanium based material, the titanium alloy is preferably used as the constituent material of the dense sheets 25 requiring the excellent strength in a constituent member of the block body 2. This is because the titanium alloy has more excellent strength. Further, examples of the titanium alloy are not limited particularly, but include an alloy in which one or more of Al, Sn, Cr, Zr, Mo, Ni, Pd, Ta, Nb, V, Pt and the like are added to Ti of a main component, and the like. Examples of such an alloy include Ti-6Al-4V, Ti-29Nb-13Ta-4.6Zr and the like.

The pair of block bodies 2 as described above is inserted between the vertebral body 101 and the vertebral body 102 (intervertebral space) side by side with each other.

By inserting the block body 2 into the intervertebral space, a space 103 is formed in an area of the intervertebral space in which no block body 2 exists. A grafted bone (in particular, autologous bone) as a filler is filled into the space 103, so that it is ensured to achieve the bone fusion between the vertebral body 101 and the vertebral body 102 through the block body 2 and the grafted bone more reliably and promptly.

Further, the spacer 1 is constituted from the pair of block bodies 2, 2. Therefore, if the arrangement of the block bodies 2, 2 is changed, that is, they are arranged in a state of spacing front ends or back ends of the block bodies 2 from each other and/or approaching them to each other, it becomes possible to treat an appropriate cure depending upon cases.

The spacer 1 as described above, for example, can be produced as follows.

<1> First, prepared is a plurality of first sheet members to become the dense sheets 25 by performing a debinding process and sintering process.

Such first sheet members can be obtained easily by preparing a sheet-shaped dense body constituted of the titanium based material and cutting the sheet-shaped dense body in a predetermined shape and size by using a slice cut method such as a laser cut method, a water jet method, a discharge wire method and an ultrasound ablation method. Alternatively, the first sheet members are prepared by using a slurry of which concentration is adjusted so that the porosity thereof is more smaller, which is the same process as those of second sheet members to become the porous sheets 21 as described later. Moreover, the first sheet members are also prepared by using a slurry of which composition and an additive amount of a foaming agent (0% to) are adjusted, which is the same process as those of the second sheet members to become the porous sheets 21 as described later.

<2> Next, prepared is a plurality of second sheet members to become the porous sheets 21 by performing a debinding process and a sintering process.

<2-1> First, prepared is a slurry containing metal powder and a foam agent.

Powder constituted of the titanium based material described above or an oxidant thereof is used as the metal powder.

Further, an average particle size of particles of the metal powder is not limited particularly, but preferably in the range of about 0.5 to 50 μm and more preferably in the range of about 3 to 30 μm. By using the metal powder including the particles having such a size, it becomes possible to set the porosity of the obtained porous sheets 21 and an average pore size of pores thereof to a predetermined value. In this regard, it is to be noted that the average particle size of the particles of the metal powder can be obtained by a laser diffractometry and the like.

An amount of the metal powder in the slurry is preferably in the range of about 30 to 80 mass % and more preferably in the range of 40 to 70 mass %. By setting the amount of the metal powder to such ranges, it becomes possible to reliably set the porosity of the obtained porous sheets 21 and the average pore size of the pores thereof to the predetermined value.

Examples of the foam agent is not limited particularly, but include a surfactant, a volatile organic solvent and the like. A water-insoluble hydrocarbon-based organic solvent having a carbon number of 5 to 8 is preferably used as the volatile organic solvent. Further, neopentane, hexane, heptanes and cyclohexane are more preferably used. The use of such a foam agent makes it possible to obtain the porous sheets 21 having a high porosity with ease.

Such a slurry contains a water-soluble resin binder and water. In addition to that, the slurry contains other components such as a plasticizer, an organic solvent and the like, if needed.

Examples of the water-soluble resin binder include methylcellulose, hydroxyl propyl methylcellulose, polyvinyl butyral, polyvinyl alcohol and the like. These materials may be used singly or in combination of two or more of them. A skeleton of the porous sheets 21 is formed well by using the slurry containing the water-soluble resin binder.

Examples of the plasticizer include glycerin, ethylene glycol, polyethylene glycol, and the like.

Examples of the organic solvent include methanol, ethanol, isopropanol, and the like.

<2-2> Next, the prepared slurry is applied onto a base in a sheet shape, then the applied slurry is heated and foamed, and thereafter is dried to obtain a green body (green sheet).

A method of molding the slurry in the sheet shape is not limited particularly, but is preferably a doctor blade method.

The heating process is not limited particularly, but is preferably performed under a high humidity atmosphere having humidity of 80% or more. By controlling a temperature condition at this time, it is possible to uniformly control pore sizes of a huge number of foam pores formed by acts of the foam agent in the whole of the slurry. As a result, it is possible to form a three dimensional skeleton constituted of the slurry containing the metal powder.

At this time, the foam pores are formed into a flat shape on a contact surface (back surface) between the slurry and the base. On the other hand, on a surface (front surface) of the slurry opposite to the base, foam pores inflated three-dimensionally due to free foam are formed. Therefore, according to the producing method as the present embodiment, a green body having an asymmetric foam structure on the back surface and the front surface each other is formed.

Further, the drying process of the slurry in which the foam pores have been formed is performed by heating at a temperature of 100° C. or less under the atmosphere or an inert gas atmosphere. This makes it possible to reliably remove moisture contained in the slurry while maintaining the foam pores included in the slurry.

<2-3> Next, the obtained green body is peeled off from the base. Thereafter, the green body is cut in the predetermined shape and size by using the slice cut method described above. The second sheet members to become the porous sheets 21 by performing the debinding process and sintering process are obtained.

<3> Next, the second sheet members (porous sheets 21 before performing the debinding process and sintering process) and the first sheet members (dense sheets 25 before performing the debinding process and sintering process) are placed so as to correspond to the shape of the block body 2 to be formed. Then, each of the second sheet members is sandwiched between the first sheet members, and thereafter they are heated in this state. By performing the debinding process and sintering process of the second sheet members and the first sheet members, a block body 2 is obtained as the porous sheets 21 and the dense sheets 25. In this regard, it is to be noted that the porosity of the dense sheets 25 after performing the debinding process and sintering process is preferably in the range of 3 to 50%.

The second sheet members and the first sheet members are debinded at a temperature within the range of about 350 to 600° C. for about 1 to 10 hours. The debinding under such conditions makes it possible to decompose and remove components other than the metal powder included in the second sheet members and the first sheet members while maintaining a foam pore structure. Consequently, it is possible to change the second sheet members and the first sheet members to a metal brown body having a skeleton structure in which the metal powder is aggregated.

Further, the second sheet members and the first sheet members (metal brown body) after performing the debinding process are sintered at a temperature within the range of about 1100 to 1350° C. for about 1 to 10 hours under a non-oxidizing atmosphere. The sintering process under such conditions makes it possible to sinter the metal powder while maintaining the foam pore structure. In addition to that, it is possible to diffuse the metal powder in the second sheet members and the first sheet members after performing the debinding process. As a result, the dense sheets 25 and the porous sheets 21 are diffusion-bonded together. Further, it is possible to sinter the metal powder while maintaining the foam pore structure, so that it is possible to obtain a block body 2 in which the dense sheets 25 and the porous sheets 21 are bonded together firmly.

In this regard, a degree of vacuum in the non-oxidizing atmosphere is preferably $5.0 \times 10^{-2}$ Pa or less. The non-oxidizing atmosphere is preferably an argon atmosphere.

Further, when the second sheet members and the first sheet members laminated with each other are heated, it is preferable to apply the stress in a direction of approaching the second sheet members and the first sheet members to each other. That is, it is preferable to compress the second sheet members and the first sheet members in a thickness direction thereof. By doing so, it is possible to reliably integrate the porous sheets 21 and the dense sheets 25.

Specifically, a pressure to be applied is preferably in the range of about 0.01 to 10 MPa and more preferably in the range of about 0.1 to 1 MPa.

As described above, the second sheet members and the first sheet members are changed to the porous sheets 21 and the dense sheets 25, respectively, by performing the debinding process and sintering process. Consequently, can be obtained the block body 2 in which the porous sheets 21 and the dense sheets 25 are bonded together firmly (integrally).

In the case where the first sheet members are constituted of the titanium based alloy (material), the porous sheets 21 (sintered second sheet members) and the first sheet members are laminated, and then the first sheet members are welded to the porous sheets 21 by laser and the like to obtain an laminated body. Thereafter, the laminated body is subjected to a heating treatment at a temperature in the range of 800 to 1050° C. for 1 to 10 hours under the non-oxidizing atmosphere (argon atmosphere or vacuum). This makes it possible to change the first sheet members to the dense sheets 25 and obtain a block body 2 by diffusion-bonding the dense sheets 25 and the porous sheets 21. In this regard, the first sheet members and the porous sheets 21 are laminated so that each surface constitutes a flat surface in the laminated body.

<Second Embodiment>

Next, description will be made on a second embodiment of a vertebral body space according to the present invention.

Figure 4:
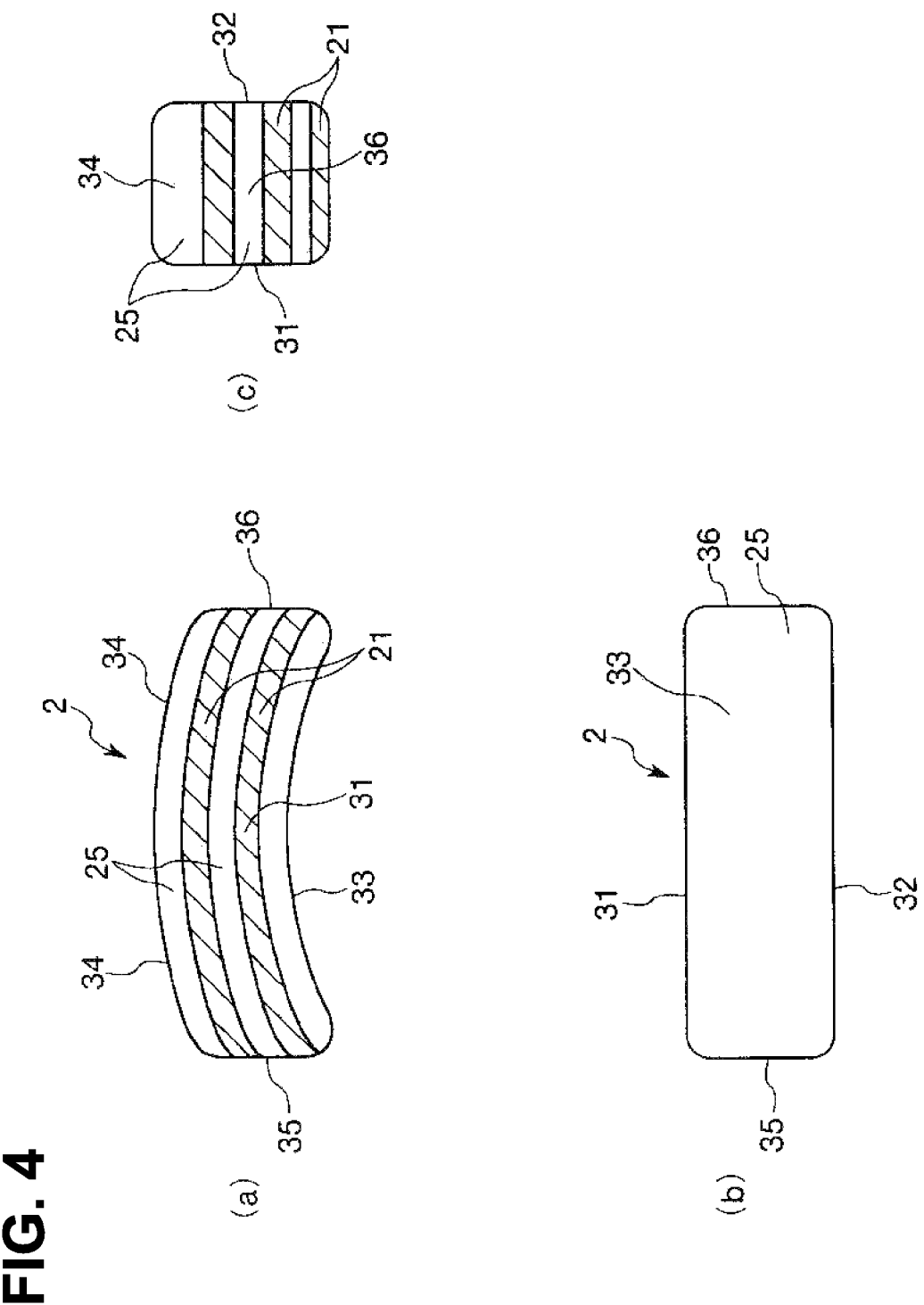
FIG. 4 is a plan view (a), a front view (b) and a side view (c) which show a second embodiment of a block body constituting a vertebral body spacer of the present invention.

FIG. 4 is a plan view (a), a front view (b) and a side view (c) which show the second embodiment of a block body constituting the vertebral body spacer of the present invention.

In the following description, the description will be made on a block body 2 shown in FIG. 4. The description will be made by focusing on different points from the block body 2 shown in FIG. 1 to FIG. 3 and the description on the common points is omitted.

The block body 2 shown in FIG. 4 is the same as the block body 2 shown in FIG. 1 to FIG. 3, except that shapes of the dense sheets 25 and the porous sheets 21 are different and a direction in which the dense sheets 25 and the porous sheets 21 are arranged is different.

In the present embodiment, the block body 2 is constituted from three dense sheets 25 and two porous sheets 21. One porous sheet 21 is sandwiched between the dense sheets 25. The direction (arranging direction) in which the dense sheets 25 and the porous sheets 21 are arranged is a direction from a right side toward a left side, namely a cross direction (short direction of the block body 2 and a direction substantially perpendicular to a direction from a first surface 31 toward a second surface 32) of the block body 2.

The dense sheets 25 and the porous sheets 21 in the block body 2 having the configuration are formed so as to correspond to a cross-section shape when the block body 2 is cut in a direction perpendicular to the direction from the right side toward the left side thereof (cross direction). Further, the dense sheets 25 and the porous sheets 21 are curved to correspond to curved shapes of surfaces 33 and 34 (block body 2).

The block body 2 of the present embodiment configured as described above can be also used as the block body 2 of the first embodiment. Further, when the block body 2 is inserted into the intervertebral space (in the inserted state), the dense sheets 25 and the porous sheets are in contact with the vertebral bodies 101, 102 alternately. Therefore, the block body 2 can exhibit the same effects as those of the block body 2 (spacer 1) of the first embodiment.

<Third Embodiment>

Next, description will be made on a third embodiment of a vertebral body space according to the present invention.

Figure 5:
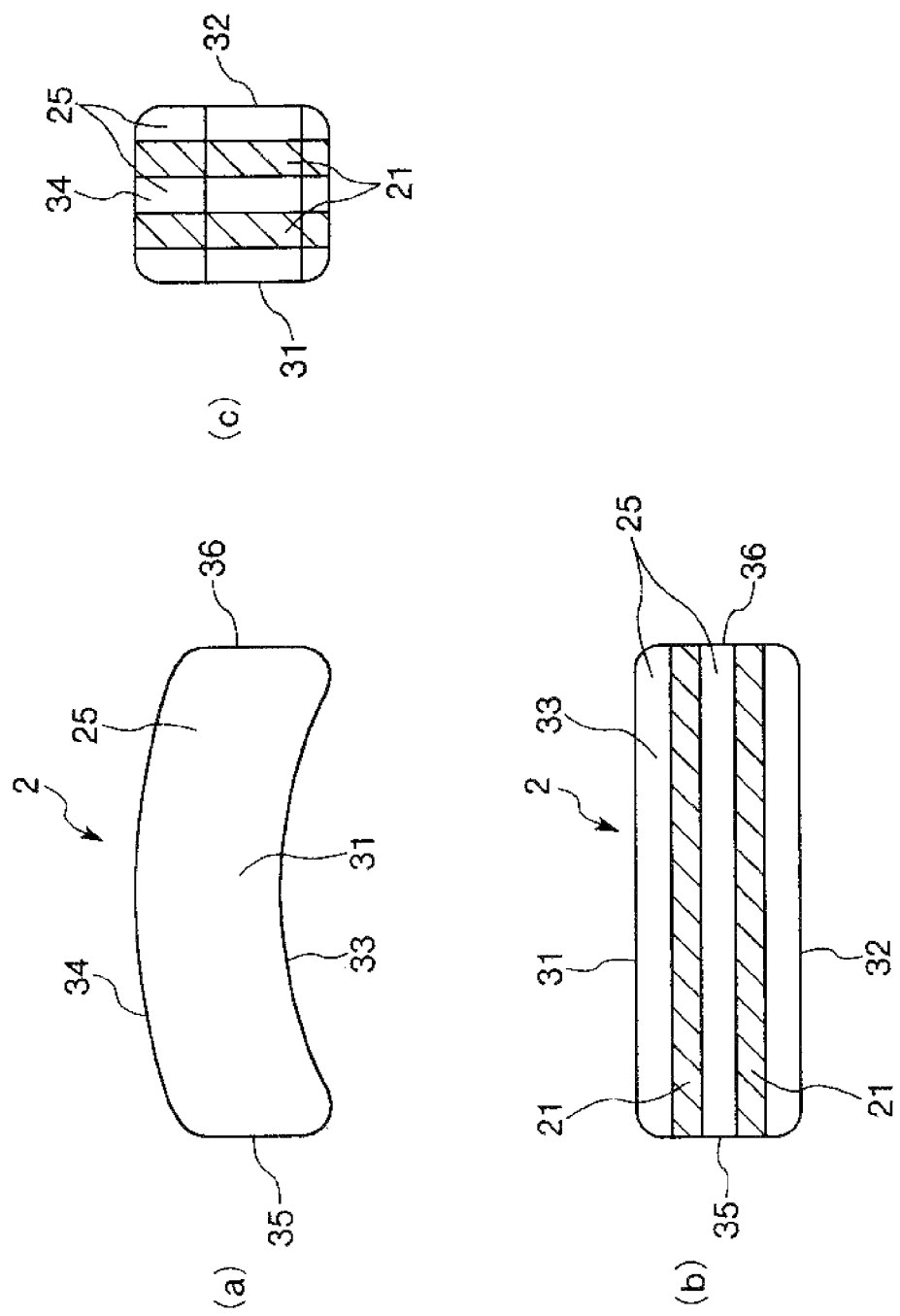
FIG. 5 is a plan view (a), a front view (b) and a side view (c) which show a third embodiment of a block body constituting a vertebral body spacer of the present invention.

FIG. 5 is a plan view (a), a front view (b) and a side view (c) which show the third embodiment of a block body constituting the vertebral body spacer of the present invention.

In the following description, the description will be made on a block body 2 shown in FIG. 5. The description will be made by focusing on different points from the block body 2 shown in FIG. 1 to FIG. 3 and the description on the common points is omitted.

The block body 2 shown in FIG. 5 is the same as the block body 2 shown in FIG. 1 to FIG. 3, except that shapes of the dense sheets 25 and the porous sheets 21 are different and a direction in which the dense sheets 25 and the porous sheets 21 are arranged is different.

In the present embodiment, the block body 2 is constituted from three dense sheets 25 and two porous sheets 21. One porous sheet 21 is sandwiched between the dense sheets 25. The direction (arranging direction) in which the dense sheets 25 and the porous sheets 21 are arranged is a direction from a head side toward a leg side, namely a thickness direction (short direction of the block body 2 and a direction substantially parallel to a direction from a first surface 31 toward a second surface 32) of the block body 2.

The dense sheets 25 and the porous sheets 21 in the block body 2 having the configuration are formed so as to correspond to a cross-section shape when the block body 2 is cut in a direction perpendicular to the direction from the head side toward the leg side thereof (thickness direction).

The block body 2 of the present embodiment configured as described above can be also used as the block body 2 of the first embodiment. Further, when the block body 2 is inserted into the intervertebral space (in the inserted state), an upper surface and a lower surface of the block body 2, which are located at the most upper side and lower side of the block body 2 and constitute flat surfaces of the dense sheets 25, are in contact with the vertebral bodies 101, 102, respectively. Therefore, the porous sheets 21 can exhibit the function as a cushion while keeping the strength of block body 2 with the dense sheets 25. This makes it possible to absorb loads of the block body 2 by the porous sheets 21 to thereby ease them. Therefore, the block body 2 can exhibit the same effects as those of the block body 2 (spacer 1) of the first embodiment. Even if backbones of cases to be applied are curved in a front or a side slightly, the block body 2 of the present invention can address to the curved state.

<Fourth Embodiment>

Next, description will be made on a fourth embodiment of a vertebral body space according to the present invention.

Figure 6:
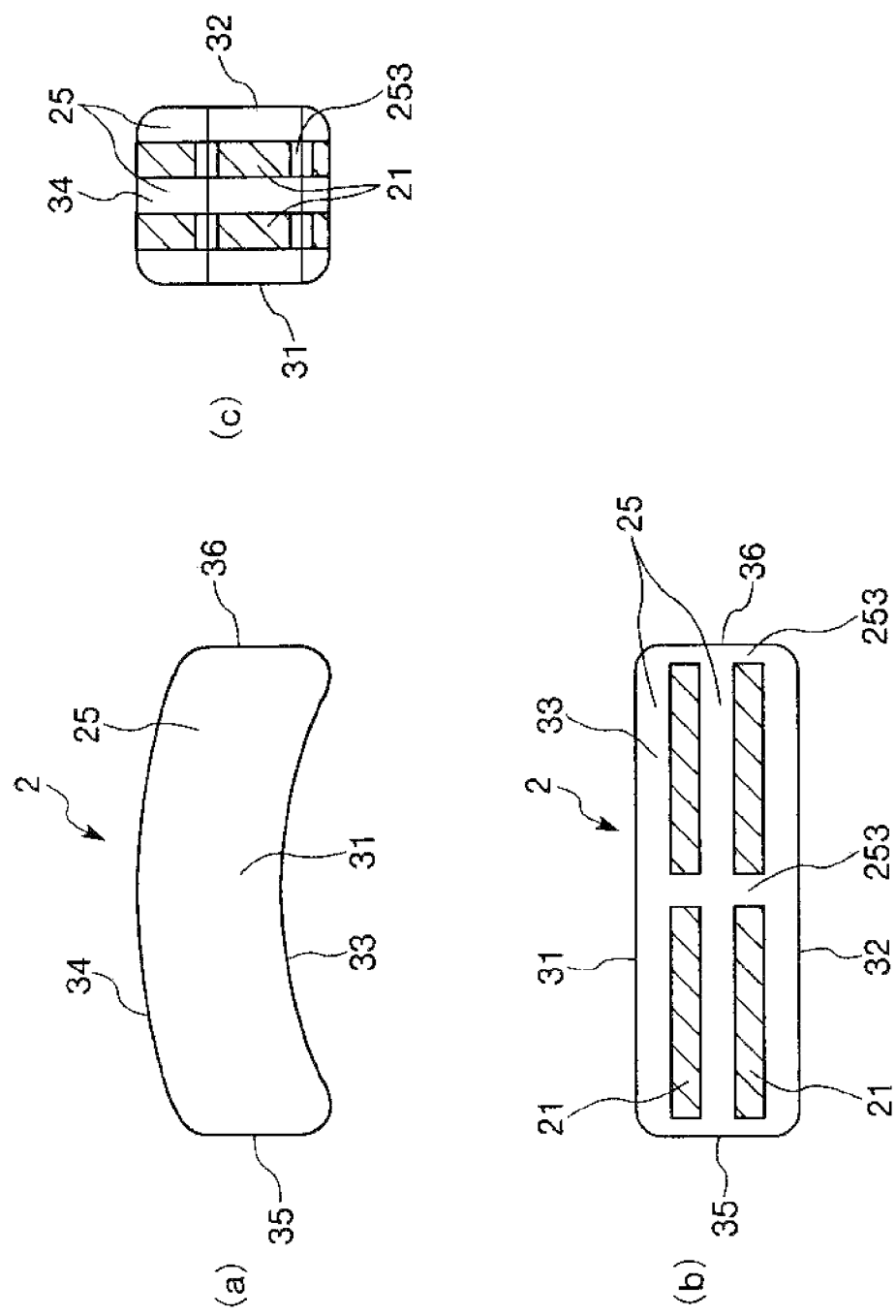
FIG. 6 is a plan view (a), a front view (b) and a side view (c) which show a fourth embodiment of a block body constituting a vertebral body spacer of the present invention.

FIG. 6 is a plan view (a), a front view (b) and a side view (c) which show the fourth embodiment of a block body constituting the vertebral body spacer of the present invention.

In the following description, the description will be made on a block body 2 shown in FIG. 6. The description will be made by focusing on different points from the block body 2 shown in FIG. 1 to FIG. 3 and the block body 2 shown in FIG. 5, and the description on the common points is omitted.

The block body 2 shown in FIG. 6 is the same as the block body 2 shown in FIG. 5, except that the block body 2 has connecting portions 253 connecting the dense sheets 25 to each other.

In the present embodiment, six connecting portions 253 are provided in total so as to surround the block body 2 along a thickness direction of the block body 2. Specifically, one connecting portion 253 is provided at each of four corner portions of the block body 2 and another connecting portion 253 is provided at a center portion of each of surfaces 33 and 34. These connecting portions 253 are provided with the dense sheets 25 integrally, and are constituted from a dense body like the dense sheets 25.

The block body 2 of the present embodiment configured as described above can be also used as the block bodies 2 of the first embodiment and the third embodiment. Further, when the block body 2 is inserted into the intervertebral space (in the inserted state), it is possible to reliably suppress or prevent the dense sheets 25 from approaching to each other due to the existence of the connecting portions 253 even if the stress is applied to the block body 2. Therefore, the block body 2 can exhibit the same effects as those of the block body 2 (spacer 1) of the first embodiment and has higher strength than that of the block body 2 of the third embodiment.

<Fifth Embodiment>

Next, description will be made on a fifth embodiment of a vertebral body space according to the present invention.

Figure 7:
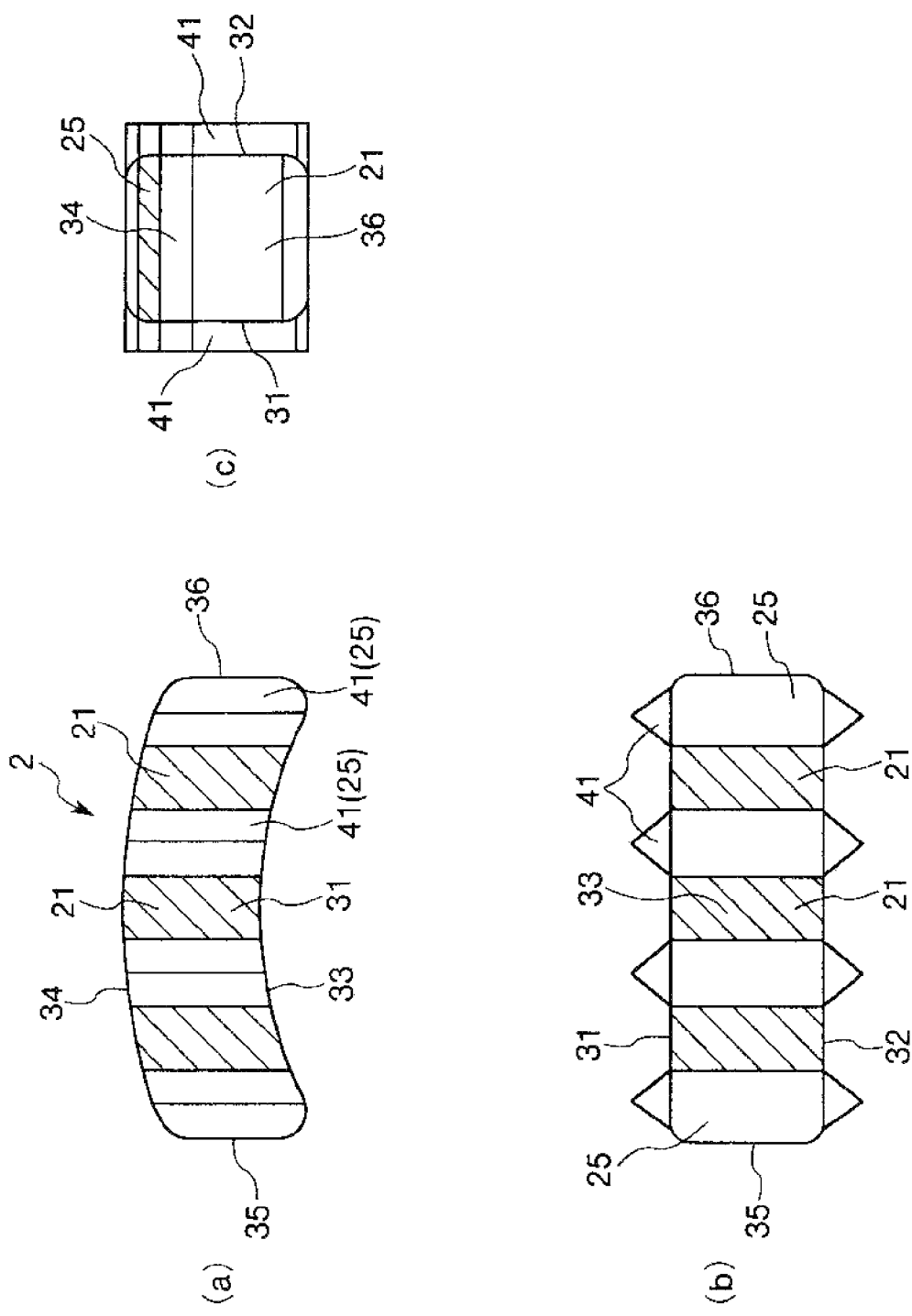
FIG. 7 is a plan view (a), a front view (b) and a side view (c) which show a fifth embodiment of a block body constituting a vertebral body spacer of the present invention.

FIG. 7 is a plan view (a), a front view (b) and a side view (c) which show the fifth embodiment of a block body constituting the vertebral body spacer of the present invention.

In the following description, the description will be made on a block body 2 shown in FIG. 7. The description will be made by focusing on different points from the block body 2 shown in FIG. 1 to FIG. 3, and the description on the common points is omitted.

The block body 2 shown in FIG. 7 is the same as the block body 2 shown in FIG. 1 to FIG. 3, except that a plurality of projection portions 41 in a triangular prism shape is provided so as to project from a first surface 31 and a second surface 32.

In the present embodiment, the plurality of projection portions 41 in the triangular prism shape in the side view is provided so as to project from the first surface 31 and the second surface 32 at positions of corresponding to the dense sheets 25. In this regard, each of the projection portions 41 is provided so that one top portion faces to the upside or the downside. As described above, the plurality of projection portions 41 projecting from the first surface 31 and the second surface 32 is provided with the block body 2. Therefore, the projection portions 41 are spiked (anchored) on the lower surface of the vertebral body 101 and the upper surface of the vertebral body 102 when the block body 2 is inserted into the intervertebral space. By doing so, it is possible to make the first surface 31 and the second surface 32 firm contact with the vertebral body 101 and the vertebral body 102, respectively. Consequently, it is possible to reliably prevent the block body 2 from dropping off from the intervertebral space.

It is preferred that the projection portions 41 configured as described above are formed from the dense sheets 25 integrally and constituted from a dense part. The projection portions 41 exhibit more excellent strength, so that it is possible to reliably prevent or suppress the projection portions 41 from being broken when the stress is applied to the block body 2 in the inserted state.

The block body 2 of the present embodiment configured as described above can be also used as the block body 2 of the first embodiment and obtain the same effects as those of the block body 2 (spacer 1) of the first embodiment.

In this regard, it is to be noted that the shape of each of the projection portions 41 is not limited to the triangular prism shape as shown in the plan view of FIG. 7, for example, it may be a pyramid shape such as a circular cone shape, a quadrangular pyramid shape or a triangular pyramid shape. In this case, the plurality of projection portions 41 in the pyramid shape is provided so as to project from the first surface 31 and the second surface 32 so that the corner portions thereof face to the upside and the downside.

<Sixth Embodiment>

Next, description will be made on a sixth embodiment of a vertebral body space according to the present invention.

Figure 8:
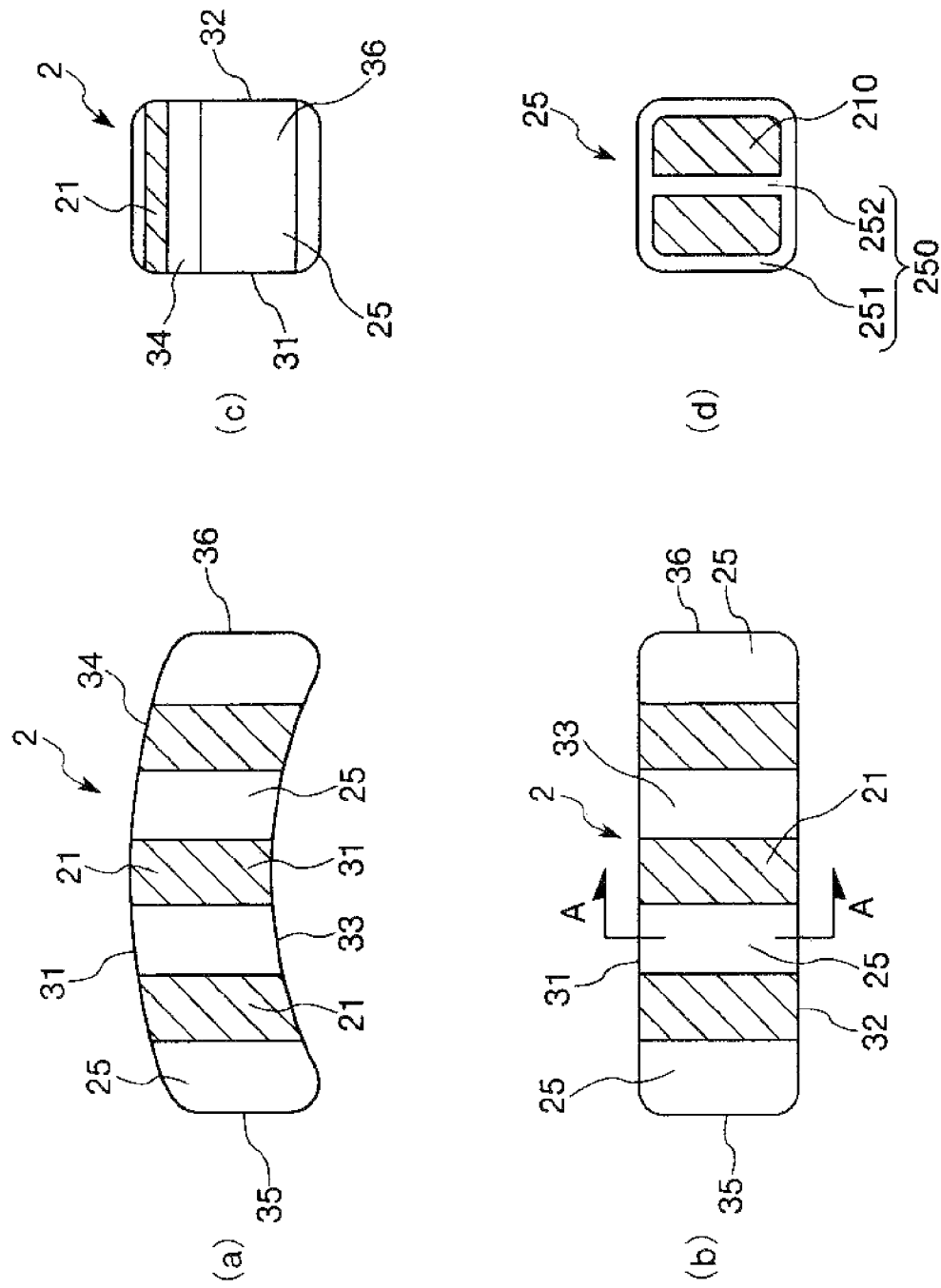
FIG. 8 is a plan view (a), a front view (b), a side view (c) and a cross-section view (d) taken along line A-A in FIG. 8(b), which show a sixth embodiment of a block body constituting a vertebral body spacer of the present invention.

FIG. 8 is a plan view (a), a front view (b), a side view (c) and a cross-section view (d) taken along line A-A in FIG. 8(b), which show the sixth embodiment of a block body constituting the vertebral body spacer of the present invention.

In the following description, the description will be made on a block body 2 shown in FIG. 8 The description will be made by focusing on different points from the block body 2 shown in FIG. 1 to FIG. 3, and the description on the common points is omitted.

The block body 2 shown in FIG. 8 is the same as the block body 2 shown in FIG. 1 to FIG. 3, except that a part of the dense sheets 25 is constituted from a dense part (dense body).

In the present embodiment, each of the dense sheets 25 has a dense part 250 and a porous part 210 provided inside it. The dense part 250 is constituted from a frame portion 251 corresponding to a circumference shape of the dense sheets 25 and a connecting portion 252 connecting parts of the frame portion 251 facing to surfaces 31 and 32 to central portions thereof. The porous part 210 is filled into a space which is formed by the frame portion 251 and the connecting portion 252.

By this configuration, the circumference parts of the dense sheets 25 are constituted from a dense part, and the inside parts thereof are constituted from a porous part. This configuration makes it possible to give excellent strength to the dense sheets 25 and firmly bond the dense sheets 25 with the adjacent porous sheets 21 in the inside of the dense sheets 25.

The block body 2 of the present embodiment configured as described above can be also used as the block body 2 of the first embodiment and obtain the same effects as those of the block body 2 (spacer 1) of the first embodiment.

<Seventh Embodiment>

Next, description will be made on a seventh embodiment of a vertebral body space according to the present invention.

Figure 9:
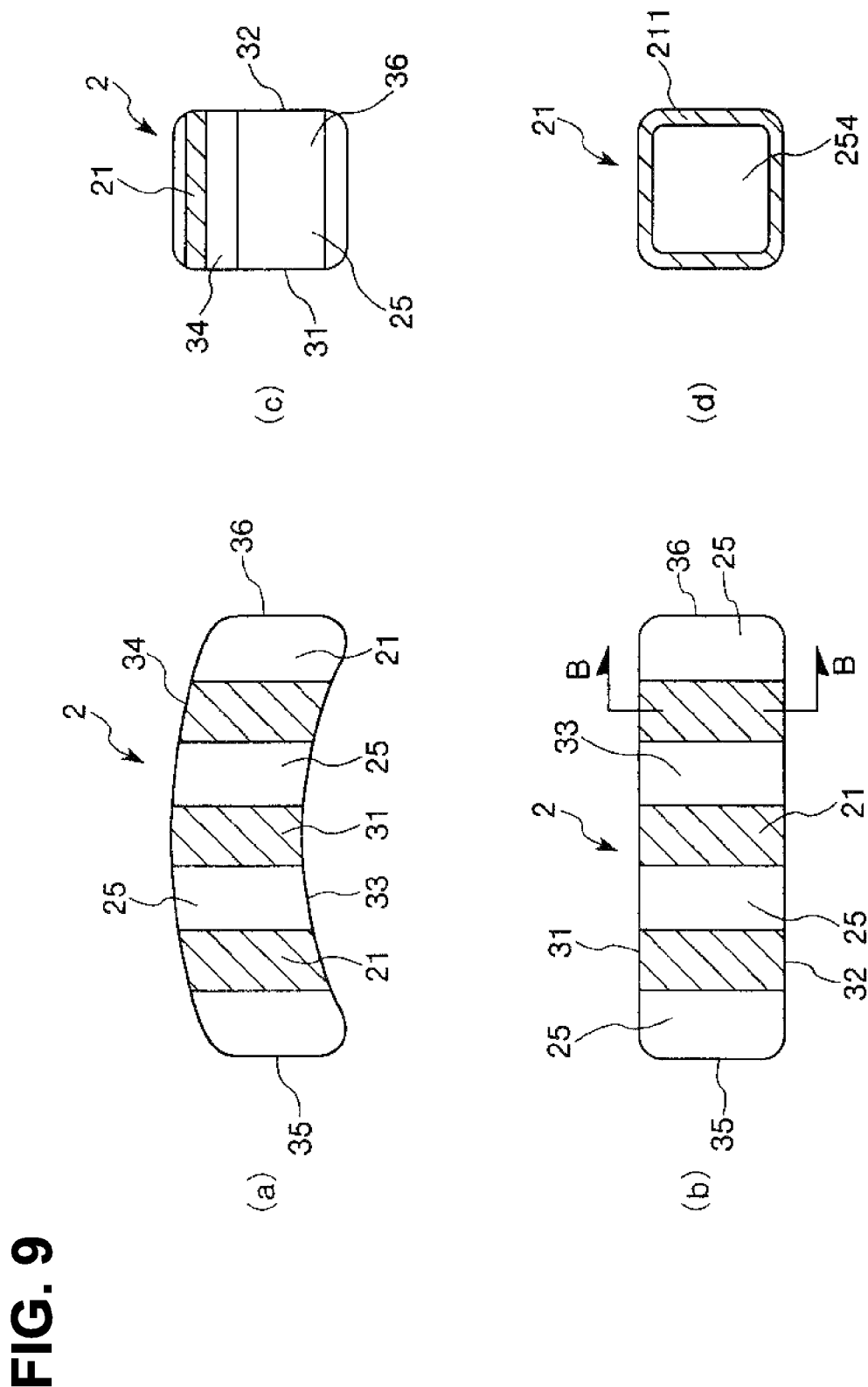
FIG. 9 is a plan view (a), a front view (b), a side view (c) and a cross-section view (d) taken along line B-B in FIG. 9(b), which show a seventh embodiment of a block body constituting a vertebral body spacer of the present invention.

FIG. 9 is a plan view (a), a front view (b), a side view (c) and a cross-section view (d) taken along line B-B in FIG. 9(b), which show the seventh embodiment of a block body constituting the vertebral body spacer of the present invention.

In the following description, the description will be made on a block body 2 shown in FIG. 9. The description will be made by focusing on different points from the block body 2 shown in FIG. 1 to FIG. 3, and the description on the common points is omitted.

The block body 2 shown in FIG. 9 is the same as the block body 2 shown in FIG. 1 to FIG. 3, except that a whole of each of the dense sheets 21 is not, but a part of the dense sheets 25 is constituted from a porous part (porous body).

In the present embodiment, the porous sheets 21 have a frame-shaped porous part 211 corresponding to a circumference shape thereof and a dense part 254 filled into a space formed at the inside of the porous part 211.

By this configuration, the circumference parts of the porous sheets 21 are constituted from a porous part, and the inside parts thereof are constituted from a dense part. This configuration makes it possible to firmly bond the porous sheets 21 and the adjacent dense sheets 25 together in the inside of the porous sheets 21.

The block body 2 of the present embodiment configured as described above can be also used as the block body 2 of the first embodiment and obtain the same effects as those of the block body 2 (spacer 1) of the first embodiment.

<Eighth Embodiment>

Next, description will be made on an eighth embodiment of a vertebral body space according to the present invention.

Figure 10:
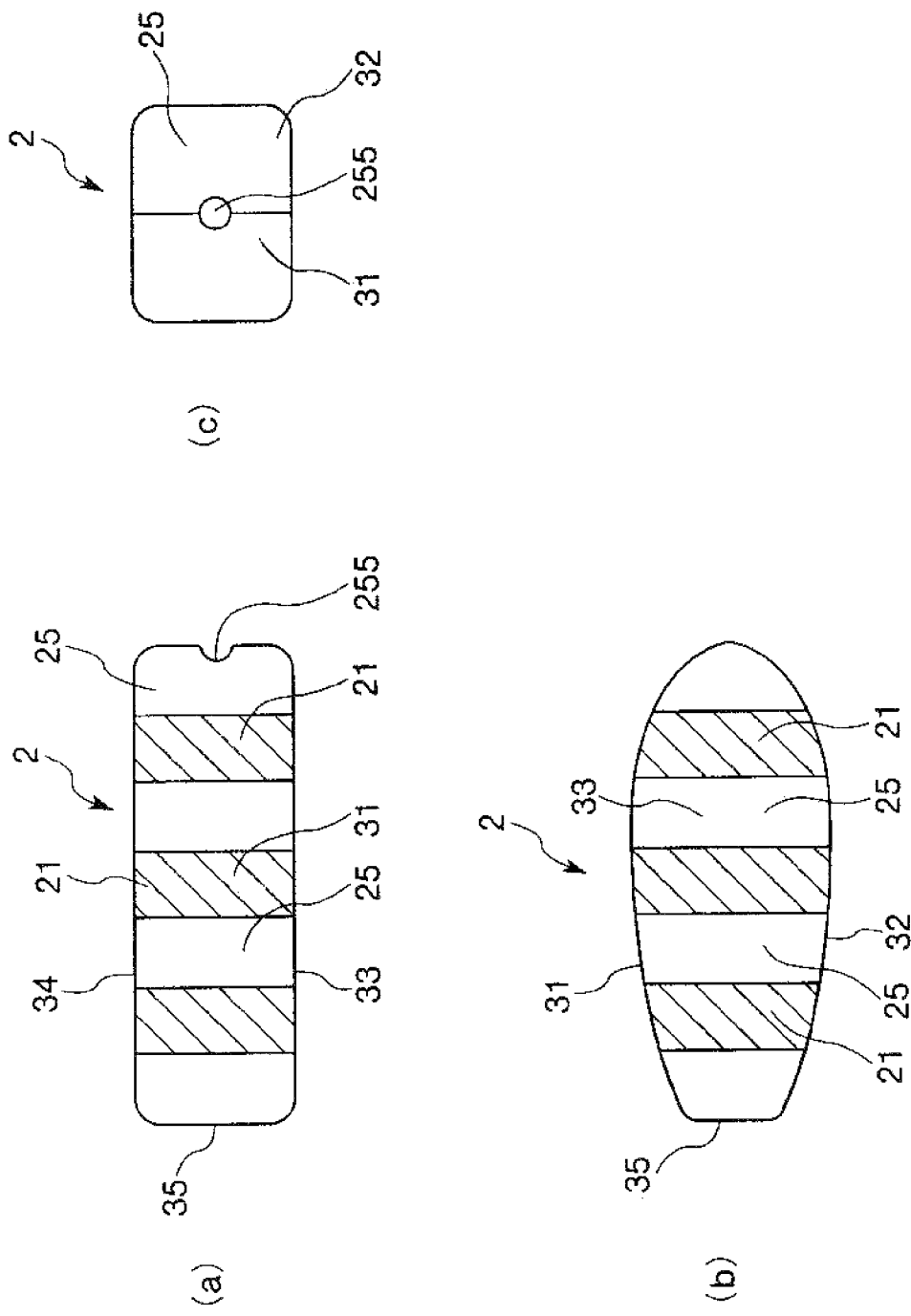
FIG. 10 is a plan view (a), a front view (b) and a side view (c) which show an eighth embodiment of a block body constituting a vertebral body spacer of the present invention.

FIG. 10 is a plan view (a), a front view (b) and a side view (c), which show the eighth embodiment of a block body constituting the vertebral body spacer of the present invention.

In the following description, the description will be made on a block body 2 shown in FIG. 10. The description will be made by focusing on different points from the block body 2 shown in FIG. 1 to FIG. 3 and the description on the common points is omitted.

The block body 2 shown in FIG. 10 is the same as the block body 2 shown in FIG. 1 to FIG. 3, except that a shape of the whole thereof is different.

In the present embodiment, both a first surface and a second surface 32 constitute a curved convex surface. The first surface 31 and the second surface 32 are connected to each other at an end portion on a front side. Thus, a sixth surface 36 is omitted. Further, each of a third surface 33, a fourth surface 34 and a fifth surface 35 constitutes substantially a flat surface. As described above, since both the first surface 31 and the second surface 32 of the block body 2 constitute the curved convex surface, it is possible to insert the block body 2 into the intervertebral space so as to slide that along the curved convex surface. For this reason, it is possible to perform an inserting operation into the intervertebral space more easily with making the block body 2 no contact with the vertebral bodies 101 and 102.

Further, in the present embodiment, a hole portion 255 is provided at a substantial center of a dense part which forms a bonding part between the first surface 31 and the second surface 32. In the case where the block body 2 is inserted into the intervertebral space by using a jig, this hole portion 255 is used to fix the block body 2 to the jig by inserting a convex portion of the jig thereinto. This makes it possible to insert the block body 2 into the intervertebral space with ease by using the jig.

The block body 2 of the present embodiment configured as described above can be also used as the block body 2 of the first embodiment and obtain the same effects as those of the block body 2 (spacer 1) of the first embodiment.

<Ninth Embodiment>

Next, description will be made on a ninth embodiment of a vertebral body space according to the present invention.

Figure 11:
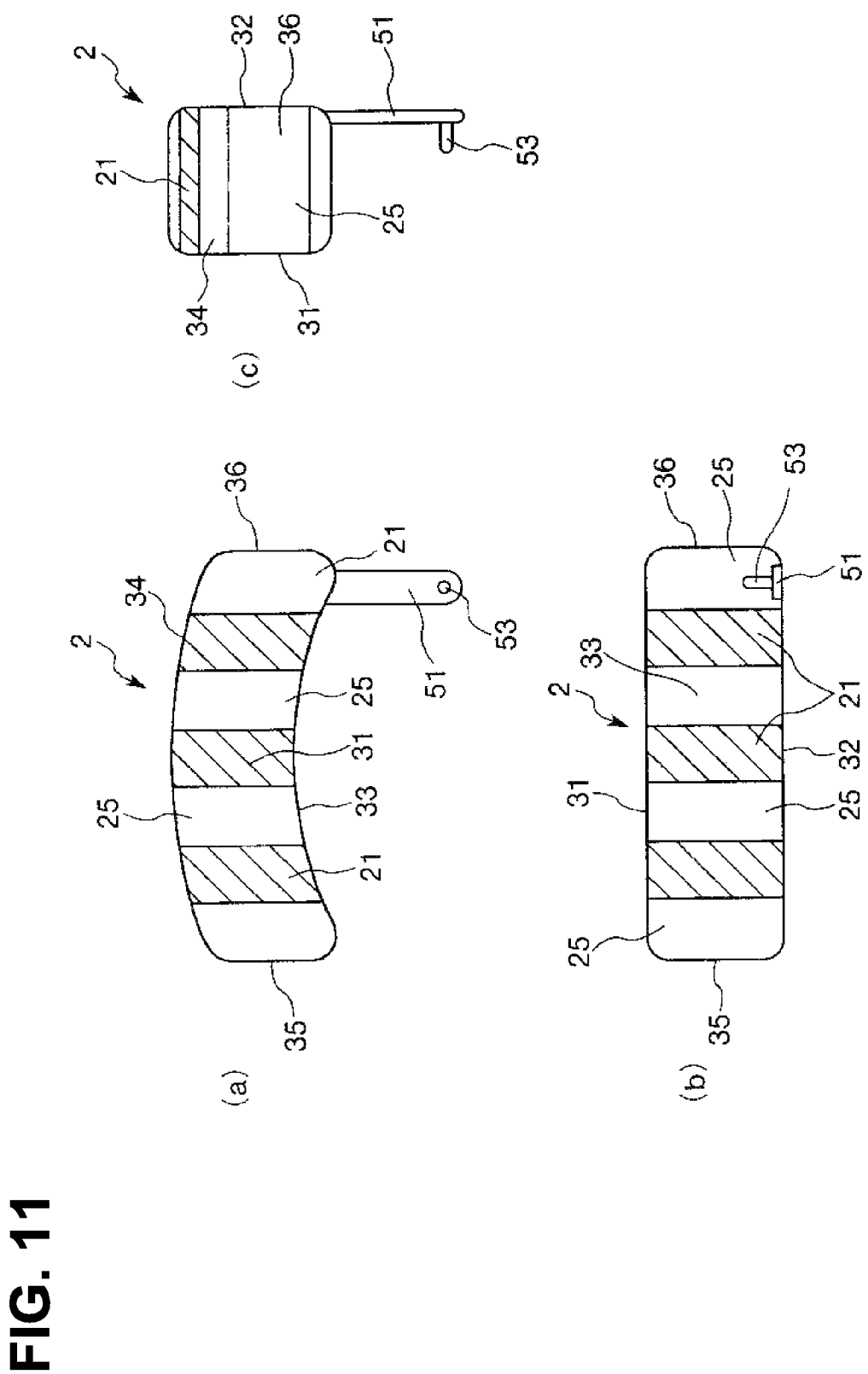
FIG. 11 is a plan view (a), a front view (b) and a side view (c) which show a ninth embodiment of a block body constituting a vertebral body spacer of the present invention.
Figure 12:
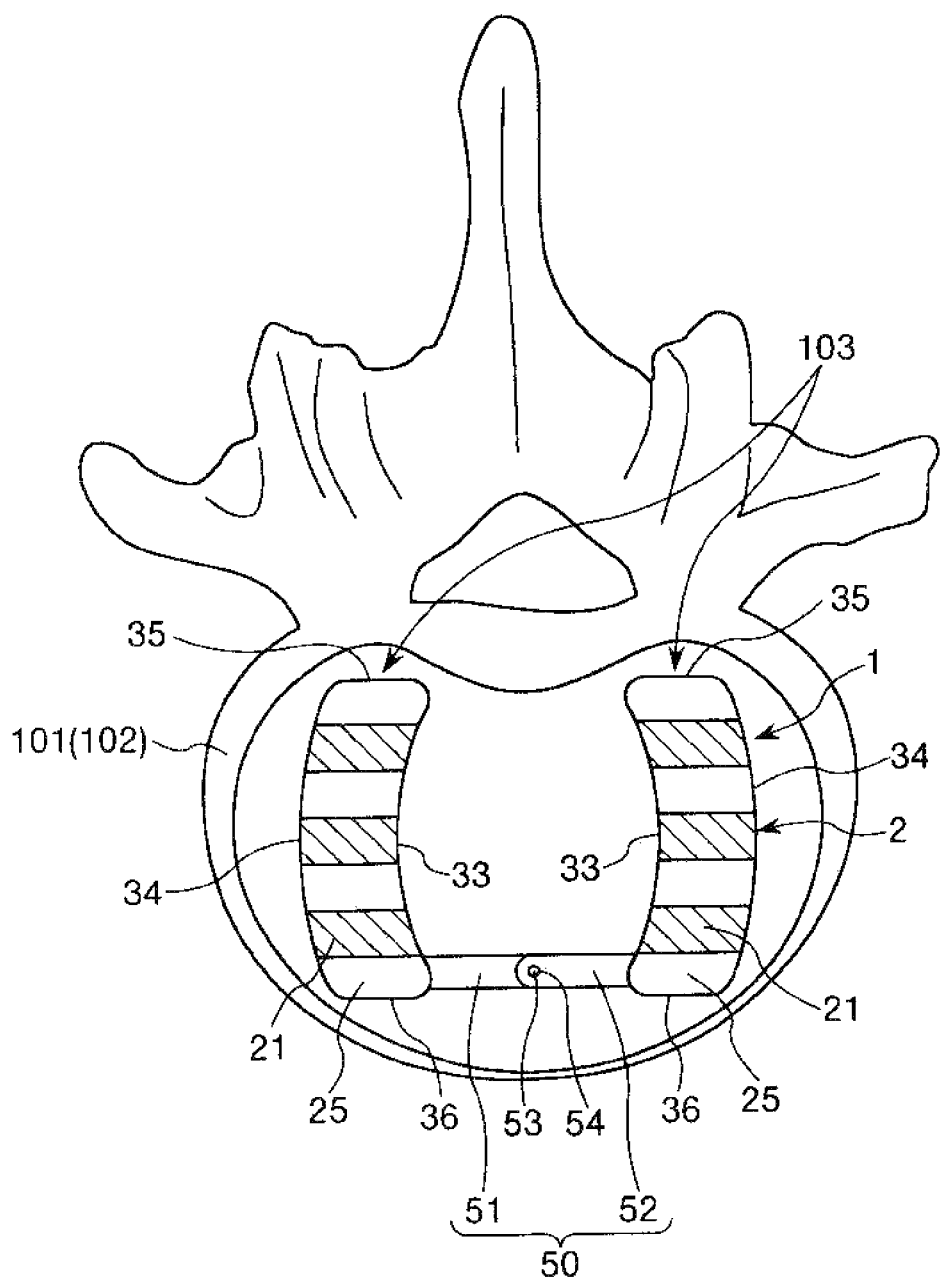
FIG. 12 is a view showing a used state of the ninth embodiment of the vertebral body spacer of the present invention.

FIG. 11 is a plan view (a), a front view (b) and a side view (c), which show a ninth embodiment of a block body constituting a vertebral body spacer of the present invention. FIG. 12 is a view showing a used state of the ninth embodiment of the vertebral body spacer of the present invention.

In the following description, the description will be made on a block body 2 shown in FIGS. 11 and 12. The description will be made by focusing on different points from the block body 2 shown in FIG. 1 to FIG. 3 and the description on the common points is omitted.

The block body 2 shown in FIG. 11 is the same as the block body 2 shown in FIG. 1 to FIG. 3, except that a connecting portion 50 of rotatably connecting a pair of block bodies 2 to each other is provided with the pair of block bodies 2.

In the present embodiment, the connecting portion 50 has a plate-shaped connection finger 51 provided at an end portion on a front side of a third surface 33 of one of the block bodies 2 and a plate-shaped connection finger 52 provided at an end portion on a front side of a third surface 33 of the other of the block bodies 2. A road-shaped body 53 is formed at an end portion on a side of the connection finger 51 opposite to the block body 2 so as to project toward an upper direction. A through hole 54 is formed at an end portion on a side of the connection finger 52 opposite to the block body 2. The two block bodies 2 are connected to each other through the connecting portion 50 by inserting the rod-shaped body 53 into the through hole 54. Further, a hinge portion is formed by inserting the rod-shaped body 53 into the through hole 54, so that it is possible for the block bodies to approach to and space from each other at the hinge portion as a center of rotation. In other words, the block bodies 2 are capable of rotating in a horizontal direction with respect to the first surface 31.

According to the spacer 1 having such an configuration, it is possible to change a position of each block body 2, namely to perform operations easily and rapidly of spacing front ends and back ends of block bodies 2 from each other and/or approaching them to each other, which depend on cases. Therefore, it becomes possible to perform an appropriate cure by using such a spacer 1 promptly. Further, since the block bodies 2 are connected to each other through the connecting portion 50, it is easy to accurately position them in the intervertebral space in the inserted state.

The block body 2 of the present embodiment configured as described above can be also used as the block body 2 of the first embodiment and obtain the same effects as those of the block body 2 (spacer 1) of the first embodiment.

The description has been made on the embodiments of the vertebral body space according to the present invention as shown in the drawings. However, the present invention is not limited to them.

For example, any configuration of the first to ninth embodiments may be combined arbitrarily in the vertebral body space according to the present invention.

Further, in each of the embodiments, the description has been made on the case of inserting the pair of block bodies 2 into the intervertebral space. However, the case is not limited thereto, and may be a case of inserting one block body 2 into the intervertebral space. In this case, the block body 2 is inserted in the front side of the intervertebral space so that the fourth surface 34 faces to the front side and the third surface 33 faces to the back side.

Moreover, the filler is not limited to the grafted bone (autologous bone), for example, may be powder of a calcium phosphate based compound and the like.

INDUSTRIAL APPLICABILITY

The vertebral body spacer of the present invention is capable of maintaining the appropriate size between vertebral bodies (intervertebral space). Further, the vertebral body spacer of the present invention is capable of reliably preventing the vertebral body spacer from being broken irrespective of the cases and the position of the intervertebral space, and thereby capable of achieving the bone fusion between the vertebral body spacer and the vertebral bodies promptly. Moreover, the space of filling the filler into the intervertebral space is ensured by inserting the vertebral body spacer thereinto. For these reasons, by filling the grafted bone to such a space, it is possible to reliably and promptly achieve the bone fusion between the vertebral bodies through the vertebral body spacer and the grafted bone. Accordingly, the present invention has industrial applicability.

What is claimed is:

1. A vertebral body spacer to be used by being inserted between vertebral bodies, comprising:
    at least one block body constituted of titanium or a titanium alloy as a main component thereof, and the block body having a pair of contact surfaces configured to contact the vertebral bodies, respectively,
    wherein the block body consists of a plurality of dense sheets of which a porosity and a thickness are identical to each other, each having a dense part on at least a peripheral portion thereof, and a plurality of porous sheets, each having a porous part on at least a peripheral portion thereof,
    wherein the plurality of dense sheets and the plurality of porous sheets are arranged alternately in a first direction so as to adjoin each other with two of the plurality of dense sheets disposed at opposed ends of the block body, and
    wherein the dense parts or the dense parts and the porous parts define the contact surfaces, and each porous part has a larger porosity than a porosity of each dense part.

2. The vertebral body spacer as claimed in claim 1, wherein the dense sheets and the porous sheets are formed integrally.

3. The vertebral body spacer as claimed in claim 1, wherein the block body is constituted from a polyhedral body defined by a plurality of surfaces including the pair of contact surfaces, and each of the plurality of surfaces constitutes a flat surface.

4. The vertebral body spacer as claimed in claim 1, wherein a whole of each of the porous sheets is constituted from the porous part.

5. The vertebral body spacer as claimed in claim 1, wherein a whole of each of the dense sheets is constituted from the dense part.

6. The vertebral body spacer as claimed in claim 1, wherein an osteoinductive factor is carried on the porous part.

7. The vertebral body spacer as claimed in claim 1, wherein the block body is formed into an elongated shape, and the first direction is a longitudinal direction of the block body.

8. The vertebral body spacer as claimed in claim 1, wherein the block body is formed into an elongated shape, and the first direction is a short direction of the block body and substantially perpendicular to a direction from one toward the other of the contact surfaces.

9. The vertebral body spacer as claimed in claim 1, wherein the block body is formed into an elongated shape, and the first direction is a short direction of the block body and substantially parallel to a direction from one toward the other of the contact surfaces.

10. The vertebral body spacer as claimed in claim 1, wherein at least one block body is constituted from a pair of block bodies.

11. The vertebral body spacer of claim 1, wherein the plurality of dense sheets includes four dense sheets, and the plurality of porous sheets includes three porous sheets.

12. The vertebral body spacer of claim 1, wherein the contact surfaces of each block body at least partially define at least one chamfered corner portion.

13. The vertebral body spacer of claim 1, wherein the porosity of each dense sheet is in the range of about 10% to about 40%.

14. The vertebral body spacer of claim 1, wherein the porosity of each porous sheet is in the range of about 50% to about 95%.

* * * * *